US009944000B2

(12) United States Patent
Smith et al.

(10) Patent No.: US 9,944,000 B2
(45) Date of Patent: Apr. 17, 2018

(54) METHODS AND DEVICES FOR APPLYING BONE CEMENT TO ORTHOPEDIC PROSTHESES TO ENHANCE BOND STRENGTH

(75) Inventors: Daniel B. Smith, Warsaw, IN (US); Timothy G. Vendrely, Fort Wayne, IN (US); Tayler E. Kreider, South Whitley, IN (US); Imad K. Merkhan, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 980 days.

(21) Appl. No.: 14/117,482

(22) PCT Filed: May 14, 2012
(Under 37 CFR 1.47)

(86) PCT No.: PCT/US2012/037786
§ 371 (c)(1),
(2), (4) Date: May 14, 2015

(87) PCT Pub. No.: WO2012/158618
PCT Pub. Date: Nov. 22, 2012

(65) Prior Publication Data
US 2015/0343684 A1    Dec. 3, 2015

Related U.S. Application Data

(60) Provisional application No. 61/485,975, filed on May 13, 2011.

(51) Int. Cl.
B29C 45/14    (2006.01)
B29C 45/26    (2006.01)
(Continued)

(52) U.S. Cl.
CPC .... *B29C 45/14336* (2013.01); *A61B 17/8841* (2013.01); *A61F 2/3094* (2013.01);
(Continued)

(58) Field of Classification Search
CPC ...... B29C 45/14065; B29C 2045/2604; B29C 45/14336; B29C 2045/1477;
(Continued)

(56) References Cited

U.S. PATENT DOCUMENTS 5,376,123 A    12/1994    Klaue et al.
6,361,731 B1    3/2002    Smith et al.
(Continued)

FOREIGN PATENT DOCUMENTS

CN    2259270 Y    8/1997
CN    106974719 A    7/2017
(Continued)

OTHER PUBLICATIONS

International Search Report, ISA/EP, Rijswijk, NL, dated Jul. 30, 2012 (4 pages).
(Continued)

Primary Examiner — Philip C Tucker
Assistant Examiner — Jimmy R Smith, Jr.
(74) Attorney, Agent, or Firm — Schwegman Lundberg & Woessner, P.A.

(57) ABSTRACT

An apparatus for forming a flowable material against a prosthetic implant can comprise a mold body having an outer surface and an inner surface. The inner surface can define a mold cavity that is selectively configured to at least partially accept the prosthetic implant in a forming position. An inlet port can be configured on the mold cavity that extends between the inner and outer surfaces. The mold cavity can substantially conform to a profile of a bone opposing surface of the prosthetic implant such that a void
(Continued)

is created between the inner surface of the mold body and the bone opposing surface of the prosthetic implant. The inlet port can be configured to permit introduction of the flowable material into the void and against the bone opposing surface of the prosthetic implant.

20 Claims, 15 Drawing Sheets

(51) Int. Cl.
| | |
|---|---|
| *B29C 45/34* | (2006.01) |
| *A61B 17/88* | (2006.01) |
| *A61F 2/30* | (2006.01) |
| *B29K 33/00* | (2006.01) |
| *B29L 31/00* | (2006.01) |

(52) U.S. Cl.
CPC .... *A61F 2/30942* (2013.01); *B29C 45/14827* (2013.01); *B29C 45/26* (2013.01); *B29C 45/34* (2013.01); *A61F 2002/30957* (2013.01); *A61F 2002/30963* (2013.01); *B29K 2033/12* (2013.01); *B29K 2901/12* (2013.01); *B29L 2031/7532* (2013.01); *F04C 2270/0421* (2013.01)

(58) Field of Classification Search
CPC .............. B29C 45/14008; B29C 45/34; B29C 45/14827; B29C 2045/4068; A61B 17/8841; A61B 17/8833; B29L 2031/7532
USPC .............. 264/275, 278, 313, 316, 334, 338; 425/436, 440, 441
See application file for complete search history.

(56) References Cited

U.S. PATENT DOCUMENTS

| | | | |
|---|---|---|---|
| 2009/0157189 A1 | 6/2009 | Hartman et al. | |
| 2009/0175978 A1* | 7/2009 | Hawkins ................. | A61F 2/30 425/214 |
| 2010/0102484 A1 | 4/2010 | Haney et al. | |

FOREIGN PATENT DOCUMENTS

| | | |
|---|---|---|
| DE | 42 28 317 A1 | 3/1994 |
| JP | 2012507343 A | 3/2012 |
| JP | 6049703 B2 | 12/2016 |
| WO | WO-2010050995 A1 | 5/2010 |
| WO | WO-2012158618 A1 | 11/2012 |

OTHER PUBLICATIONS

Written Opinion of the ISA, ISA/EP, Rijswijk, NL, dated Jul. 30, 2012 (7 pages).
Written Opinion of the International Preliminary Examining Authority dated Apr. 29, 2013 (7 pages).
International Preliminary Report on Patentability, IPEA/EP, Munich, dated Aug. 22, 2013 (7 pages) with accompanying annexes (15 pages).
"Australian Application Serial No. 2012255975, First Examiner Report dated Oct. 18, 2015", 2 pgs.
"Australian Application Serial No. 2012255975, Response filed Feb. 12, 2016 to First Examiner Report dated Oct. 18, 2015", 16 pgs.
"Chinese Application Serial No. 2012800234978, Office Action dated May 12, 2016", w/ English Translation, 10 pgs.
"Chinese Application Serial No. 2012800234978, Office Action dated Nov. 30, 2015", w/ English Translation, 12 pgs.
"Chinese Application Serial No. 2012800234978, Response filed Jan. 29, 2016 to Office Action dated Nov. 30, 2015", w/ English Translation, 6 pgs.
"Chinese Application Serial No. 2012800234978, Response filed Jul. 14, 2016 to Office Action dated May 12, 2016", w/ English Claims, 16 pgs.
"Chinese Application Serial No. 2012800234978, Response filed Sep. 8, 2015 to Office Action dated Apr. 7, 2015", w/ English Claims, 11 pgs.
"Chinese Application Serial No. 2012800234978, Voluntary Amendment filed Jul. 10, 2014", w/ English Claims, 10 pgs.
"European Application Serial No. 12723043.1, Response filed Jun. 17, 2014 to Office Action dated Jan. 22, 2014", 10 pgs.
"European Application Serial No. 14172750.3, Response filed Feb. 20, 2015 to Office Action dated Aug. 25, 2014", 21 pgs.
"International Application Serial No. PCT/US2012/037786, International Preliminary Report on Patentability dated Oct. 21, 2013", 23 pgs.
"International Application Serial No. PCT/US2012/037786, International Search Report dated Jul. 30, 2012", 4 pgs.
"International Application Serial No. PCT/US2012/037786, Written Opinion dated Jul. 30, 2012", 6 pgs.
"Japanese Application Serial No. 2014-510539, Office Action dated Mar. 11, 2016", W/ English Translation, 5 pgs.
"Japanese Application Serial No. 2014-510539, Response filed Jun. 13, 2016 to Office Action dated Mar. 11, 2016", w/ English Claims, 12 pgs.
Office Action dated Apr. 7, 2015 in corresponding Chinese Patent Application No. 201280023497.8 with English summary letter.
"European Application Serial No. 14172750.3, Communication Pursuant to Article 94(3) EPC dated Nov. 14, 2016", 4 pgs.
"European Application Serial No. 12723043.1, Response filed Apr. 7, 2017 to Office Action dated Dec. 5, 2017", 12 pgs.
"European Application Serial No. 14172750.3, Response filed Mar. 24, 2017 to Office Action dated Nov. 14, 2016", 22 pgs.
Extended European Search Report and Search Opinion dated Aug. 25, 2014 in related EP Application No. 14172750.3-1654.

* cited by examiner

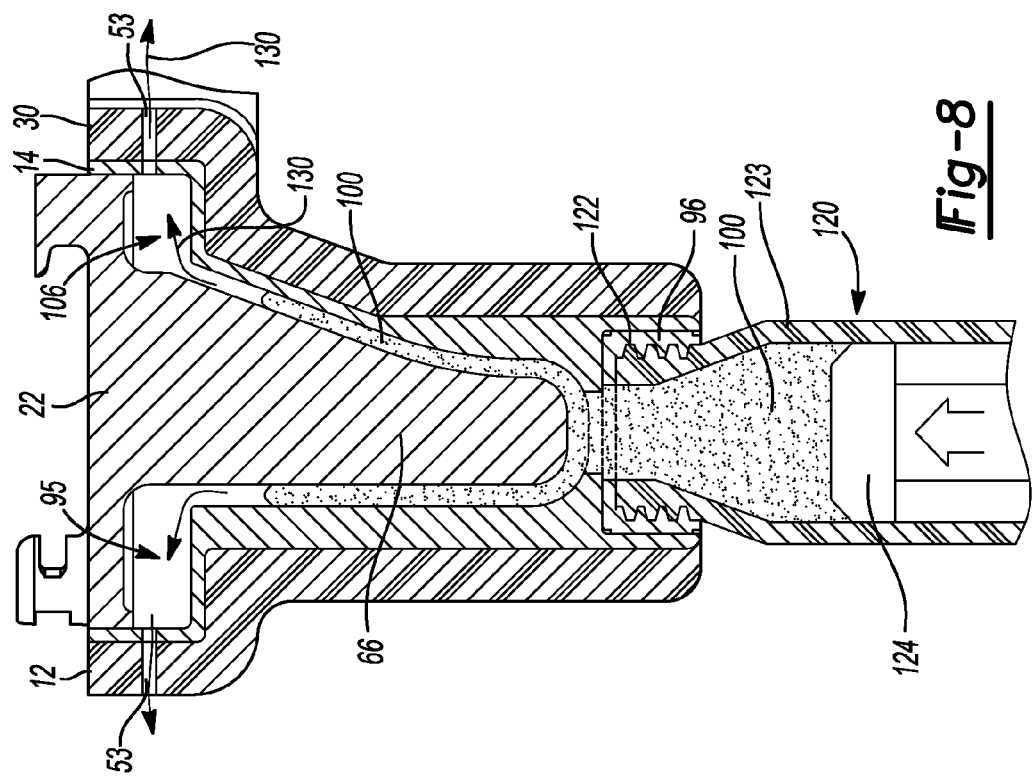
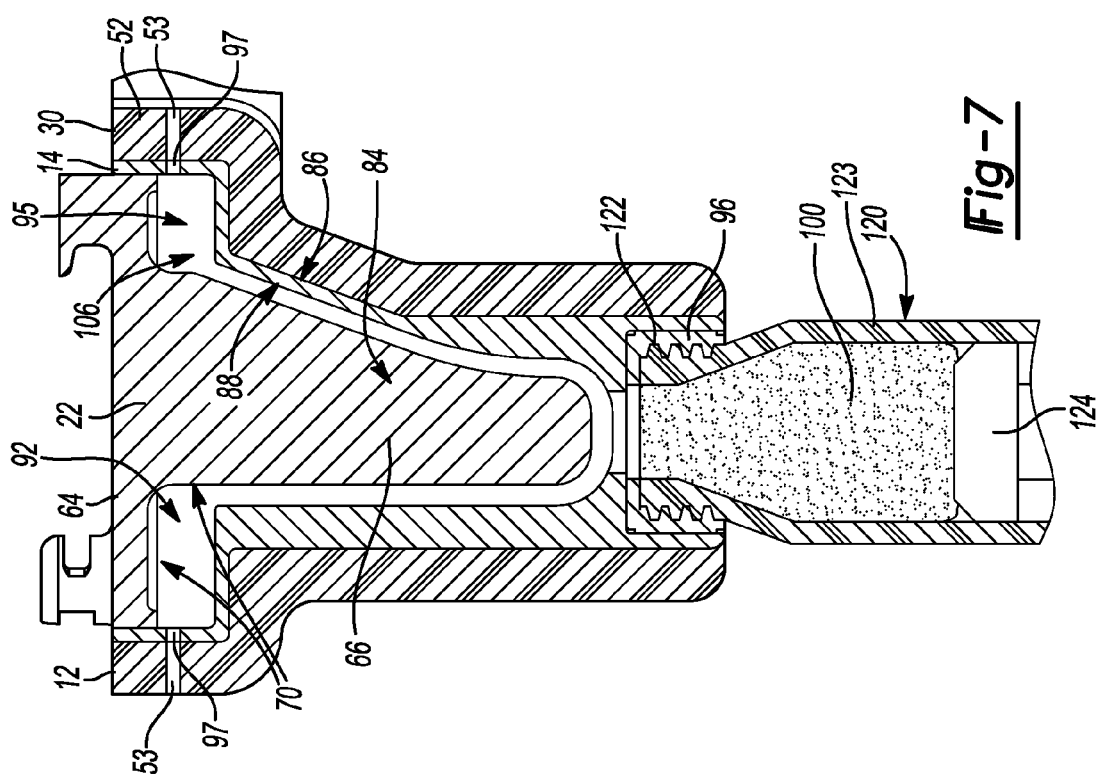

METHODS AND DEVICES FOR APPLYING BONE CEMENT TO ORTHOPEDIC PROSTHESES TO ENHANCE BOND STRENGTH

CROSS-REFERENCE TO RELATED APPLICATIONS

This application is a 371 National Phase application of International Application PCT/US2012/037786, filed May 14, 2012, which claims the benefit of U.S. Provisional Application No. 61/485,975, filed on May 13, 2011. The entire disclosures of the above applications are incorporated herein by reference.

INTRODUCTION

The present disclosure relates generally to orthopedic implants that incorporate bone cement between the implant and the opposing bone surface, and more specifically, to a mold body and related method for forming a flowable material against the orthopedic implant prior to implantation.

In many examples, it may be desirable to incorporate bone cements such as polymethylmethacrylate (PMMA) between the bone opposing surface of the implant and the host bone. In this regard, such bone cements can offer an adhesive property to further couple the implant to the host bone. Cement bond strength can be a function of both true adhesion and micro-mechanical interlock that can be established between the cement and the bone opposing surface of the implant (in some examples such as a grit-blasted or porous metal surface). Micro-mechanical interlock is influenced significantly by cement viscosity, with very high viscosity cements lacking the ability to establish a superior micro-mechanical interlock. Both pre-dough or doughy cement surfaces that have been exposed to air for a period of time can form a leathery skin via monomer liquid evaporation. These leathery surfaces can be especially poorly suited to forming a good micro-mechanical interlock, have no adhesive properties and may be incapable of forming a durable bond with the implant.

Bone cement can sometimes be applied to a prepared bone at the implantation site first. Sometimes, bone cement may be applied to the implant prior to placing it. Other times, a combination of these cement application methods may be used. In the interest of time and minimizing mess, it can be advantageous to use doughy cement regardless of the technique employed. However, the use of very doughy cement, and especially cement on which a leathery skin has formed, can result in sub-optimal cement-prosthesis interface quality. Application of low viscosity or medium viscosity cement directly to implants is not practical as it typically runs off of the implant. As a result, a surgeon must try to balance time, mess, and interface quality.

SUMMARY

This section provides a general summary of the disclosure, and is not a comprehensive disclosure of its full scope or all of its features.

An apparatus for forming a flowable material against a prosthetic implant can comprise a mold body having an outer surface and an inner surface. The inner surface can define a mold cavity that is selectively configured to at least partially accept the prosthetic implant in a forming position. In some embodiments, an inlet port is configured on the mold cavity that extends between the inner and outer surfaces. The mold cavity can substantially conform to a profile of a bone opposing surface of the prosthetic implant (i.e., the surface of the implant which is facing, but not necessarily in direct contact with, the bone) such that a void is created between the inner surface of the mold body and the bone opposing surface of the prosthetic implant. The inlet port can be configured to permit introduction of the flowable material into the void and against the bone opposing surface of the prosthetic implant.

According to other features, the mold body can further define at least one vent formed through the inner and outer surfaces. The vent can be configured to permit air to escape therethrough upon the introduction of the flowable material into the void. The mold body can be formed of a rigid material or a semi-rigid material. In one example, the mold body can be formed of silicone, polyethylene, polycarbonate, polyethylene terephthalate (PET), or polypropylene.

According to additional features, the mold body can comprise at least one tab extending from a perimeter wall thereof. The at least one tab can have an engaging lip that is configured to engage the prosthetic implant and maintain the prosthetic implant within the mold cavity during the introduction of the flowable material. The perimeter wall of the mold body can define slits on opposite sides of the at least one tab. The slits can facilitate the at least one tab from being selectively broken away from the remainder of the mold body. The mold body can further comprise a pair of ears that define passages and extend from a perimeter wall of the mold body. The apparatus can further comprise a locking bar that is removably received into the passages. The locking bar can further comprise a shaft and an engagement head. The engagement head can comprise structure that selectively engages complementary structure provided on the prosthetic implant for imparting a removal force onto the prosthetic implant from the mold body. The locking bar can also be used for positioning of the implant during implant placement to avoid contact with cement.

According to still other features, the apparatus can further include a membrane that is removably disposed on the inner surface of the mold cavity. The membrane can be flexible. The membrane can comprise at least one of a slit, thin section, perforations, and a tear-starting notch. The membrane can comprise at least one flap that extends from a periphery and is configured to facilitate removal of the membrane from one of the mold and prosthetic implant. The membrane can be formed of silicone. In some examples, the membrane can be peeled from the cement.

The mold cavity can further comprise a first cavity portion having a geometry that corresponds to a first feature of the prosthetic component and a second cavity portion having a geometry corresponding to a second feature of the prosthetic component. The prosthetic component can comprise a tibial tray. The first feature can comprise a platform portion of the tibial tray. The second feature can comprise a stem of the tibial tray. At least one of the mold body and membrane can include a vacuum port formed therethrough.

A kit for forming a flowable material against a prosthetic implant can include a prosthetic component having a bone opposing surface. The kit can further comprise a mold body having an outer surface and an inner surface. The inner surface can define a mold cavity that is selectively configured to at least partially accept the prosthetic implant in a forming position. An inlet port can be configured on the mold body that extends between the inner and outer surfaces. The mold cavity can substantially conform to a profile of the bone opposing surface of the prosthetic implant such that a void is created between the inner surface of the mold body and the bone opposing surface of the prosthetic implant.

A method for forming a flowable material against a prosthetic implant can comprise locating the prosthetic implant at least partially into a mold cavity thereby creating a void between a bone opposing surface of the prosthetic implant and an inner surface of the mold cavity. The flowable material having a first viscosity can be introduced into the void and against the bone opposing surface of the prosthetic implant. A predetermined amount of time is allowed to pass until the flowable material has adhered to the bone opposing surface of the prosthetic implant and has a second viscosity that is higher than the first viscosity. The flowable material in the second viscosity can have a doughy texture. The prosthetic implant with the flowable material having the doughy texture adhered to the bone opposing surface can then be removed from the mold cavity.

The prosthetic implant can be located at least partially into the mold cavity by positioning a membrane intermediate the inner surface of the mold cavity and the bone opposing surface of the prosthetic implant. The method can further comprise coupling a flowable material delivery device to an inlet port on the mold body. The method can further include actuating the flowable material delivery device thereby introducing the flowable material having the first viscosity into the void and against the bone opposing surface of the prosthetic implant. During introduction of the flowable material, air can be released from the void through vent ports formed through the mold body during the introduction of the flowable material. The prosthesis can then be removed from the mold. The method can further include peeling the membrane from the flowable material having the second viscosity subsequent to removing the prosthetic implant and flowable material having the doughy texture from the mold cavity.

According to some features, introducing the flowable material having the first viscosity can comprise introducing the flowable bone cement against a bone opposing surface of a tibial component. Locating the prosthetic implant at least partially into a mold cavity can further comprise locating a platform portion of the tibial component into a first cavity portion of the mold cavity and locating a tibial stem of the tibial component into a second cavity portion of the mold cavity.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 7-9 illustrate an exemplary sequence of introducing a flowable material into a void created between the prosthetic implant and the membrane.

Corresponding reference numerals indicate corresponding parts throughout the several views of the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Figure 1:
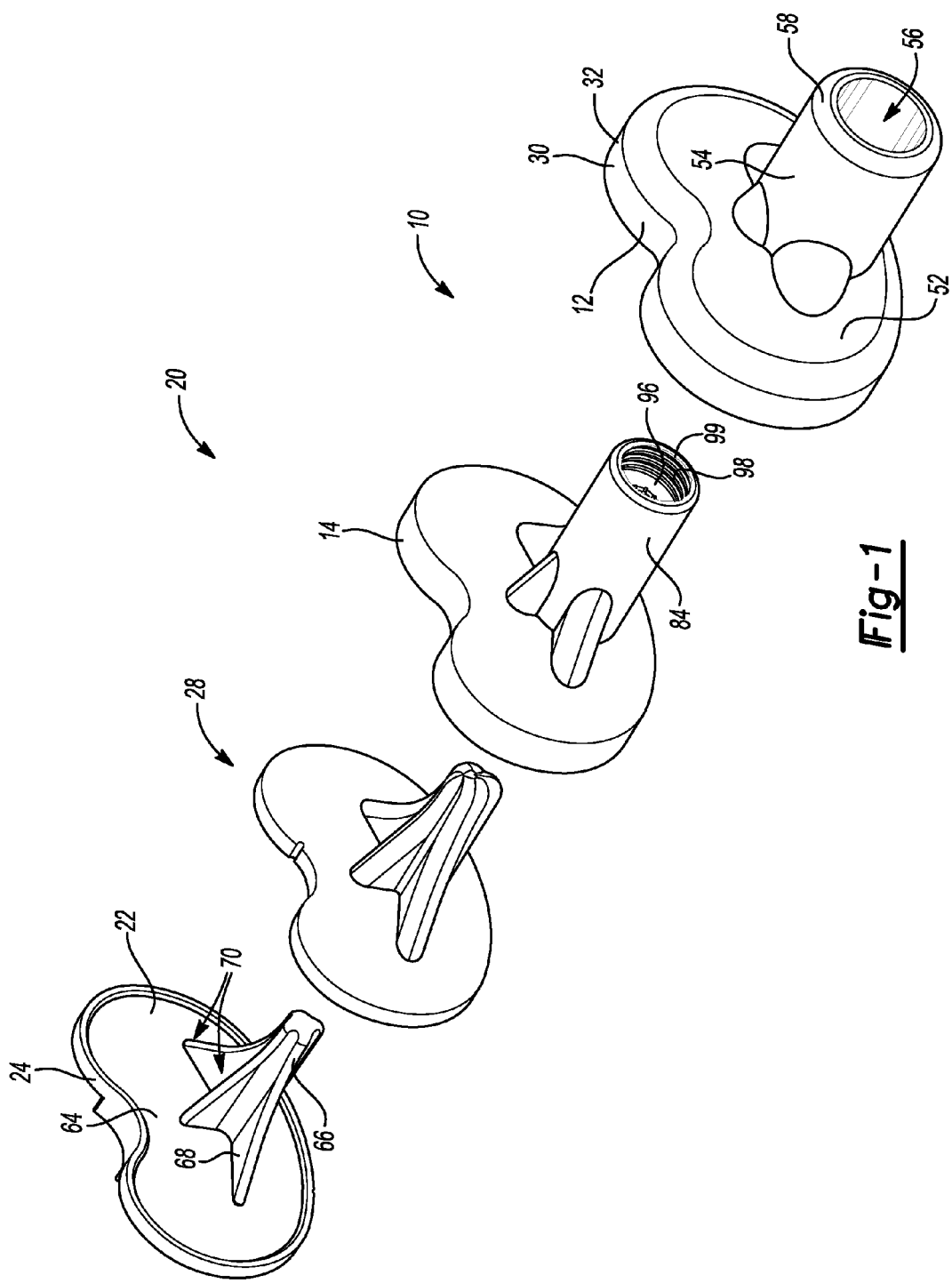
FIG. 1 is a perspective view of an exemplary kit constructed in accordance to the present teachings that includes a prosthetic implant, a dough-like structure, a membrane, and a mold.
Figure 2:
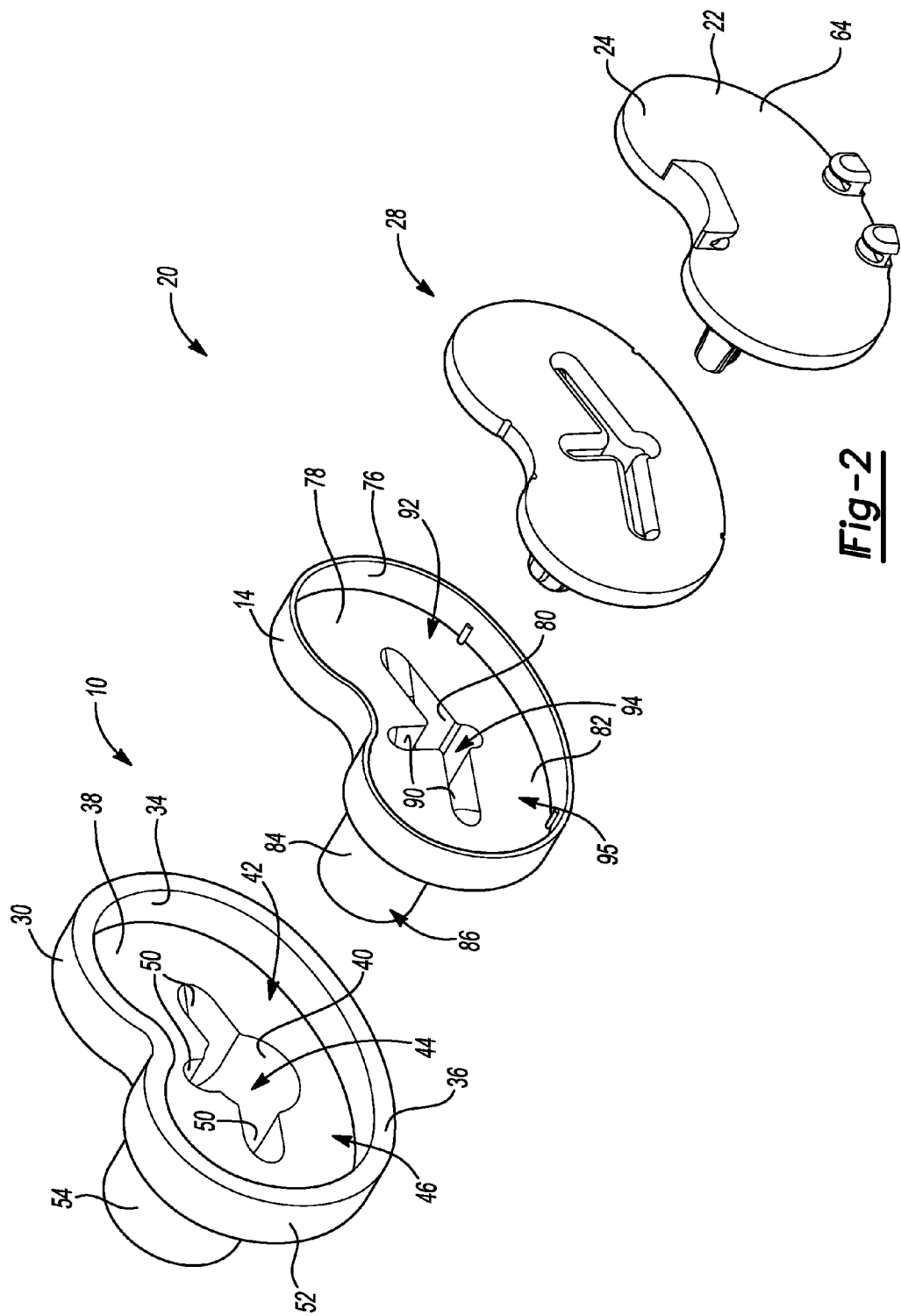
FIG. 2 is a perspective view of the kit of FIG. 1.
Figure 3:
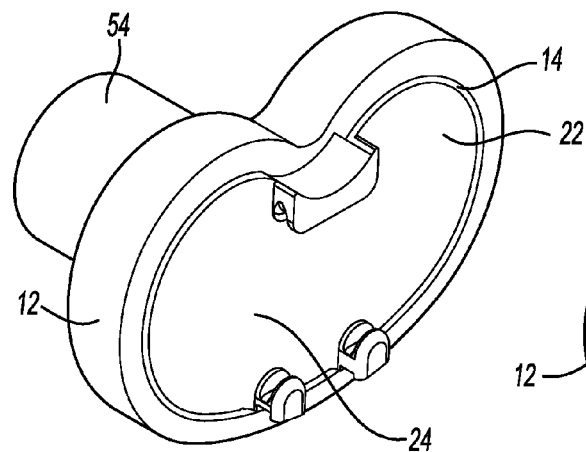
FIG. 3 is a perspective view of the prosthetic implant and membrane shown received into a cavity of the mold.
Figure 4:
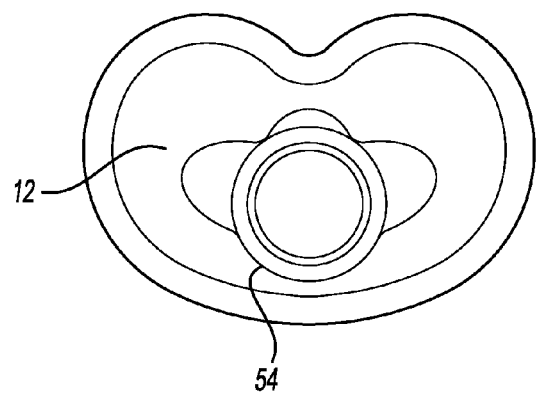
FIG. 4 is a bottom plan view of the mold of FIG. 1.
Figure 5:
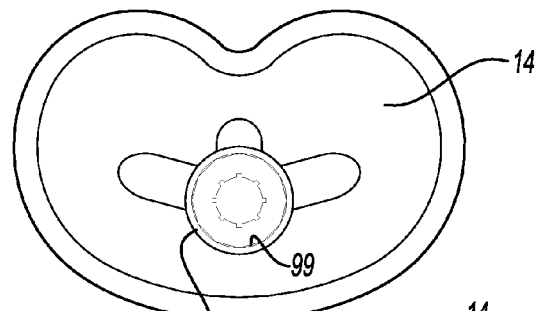
FIG. 5 is a bottom plan view of the membrane of FIG. 1.
Figure 6:
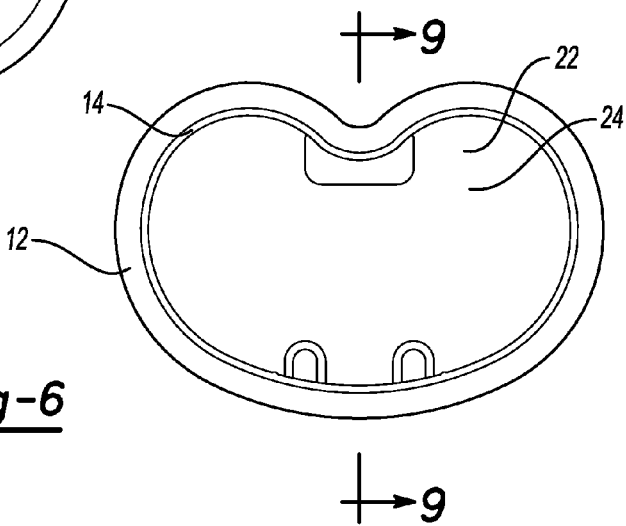
FIG. 6 is a top plan view of the prosthetic implant, membrane, and mold of FIG. 3.

With initial reference to FIGS. 1 and 2, an exemplary apparatus for forming a flowable material against a prosthetic implant is shown and generally identified at reference numeral 10. The flowable material described herein is bone cement such as, but not limited to, polymethylmethacrylate (PMMA bone) cement. Bone cements include those formed from a methyl methacrylate monomer and poly (methyl methacrylate), methyl methacrylate-methyl acrylate copolymer or methyl methacrylate-styrene copolymer. Such cements are generally made from mixing two components, usually during the clinical procedure, resulting in a composition which hardens over time. The cement components may comprise a powder component, comprising a polymer selected from homopolymers or copolymers of acrylic acid esters, methacrylic acid esters, styrene, and mixtures thereof. The cement components may further comprise a reactive liquid comprising reactive organic monomers selected from methylmethacrylate, homolog esters of methacrylic acid or their mixtures. Cements among those useful herein include Palacos R, Cobalt HV, SmartSet HV, Simplex P, Cobalt MV, and SmartSet MV.

The apparatus 10 can generally include a mold 12 and a membrane 14. According to some examples as discussed herein, the apparatus 10 can be provided as part of a kit 20 that can further include a prosthetic implant 22. The prosthetic implant 22 discussed herein includes a tibial component 24. It will be appreciated, however, that the various features and methods disclosed herein may be also used for forming a flowable material against other prosthetic implants such as knee femoral and patellar components, hip stems, acetabular cups, glenoid components, ulnar components, and other prosthetic implants that may require the use of bone cement between a bone opposing surface of the prosthetic implant and the corresponding bone surface of the host bone. As will become appreciated from the following discussion, the apparatus 10 can be used to introduce a flowable material (such as bone cement) having a first viscosity to a location against the prosthetic implant 22. The mold 12 and, in some examples, together with the membrane 14, can cooperate to form the flowable material into a doughy cement or dough-like structure generally identified at reference numeral 28. The dough-like structure 28 is illustrated in exploded view simply for illustration purposes with the understanding that the dough-like structure 28 will have a second viscosity greater than the first viscosity and be adhered to or otherwise coupled to the tibial component 24.

With continued reference now to FIGS. 1 and 2, additional features of the mold 12 will now be described. The mold 12 can generally comprise a mold body 30 having an outer surface 32 and an inner surface 34. The mold body 30 can generally include a perimeter wall 36, an end wall 38, and an elongated wall 40. The perimeter wall 36 and the end wall 38 can cooperate to define a first cavity portion 42. Similarly, the elongated wall 40 can define a second cavity portion 44. The first cavity portion 42 and the second cavity portion 44 can collectively define a mold cavity 46 of the mold body 30.

The elongated wall 40 can generally include fin receiving extension walls 50. While the fin receiving extension walls 50 are shown having a particular geometry, the fin receiving extension walls 50 can have other geometries such as cylindrical, splined or I-beam for example. As will become appreciated, the first cavity portion 42 can have a geometry that substantially conforms to a tray portion of the tibial component 24. Similarly, the second cavity portion 44 can generally provide a geometry that substantially conforms to a stem extending from the tibial component 24. The perimeter wall 36 and the end wall 38 can cooperate to form a tray receiving portion 52. Vent ports 53 (FIG. 7) can be formed through the mold body 30.

The elongated wall 40 can provide a stem receiving portion 54. An inlet port 56 can be formed on a distal end 58 of the stem receiving portion 54. In various examples, the mold body 30 can be formed of a rigid material, i.e., a material having sufficient rigidity to contain and define the cement material in a pre-determined shape forming a void around at least a portion of an implant, as further described below. Preferably, the material of the mold 14 is transparent or translucent. In this regard, a surgeon or medical technician can view the interior of the mold during introduction of flowable material. Suitable materials include polyethylene, polycarbonate, polyethylene terephthalate (PET), polypropylene, or silicone.

The tibial component 24 can generally include a platform-like tray 64 and a stem 66. The stem 66 can comprise a series of fins 68 extending therefrom. The outer surface of the stem 66 and an underside surface of the platform-like tray 64 can collectively provide a bone opposing surface 70. Again it will be appreciated that the particular geometry of the tibial component 24 is merely exemplary.

The membrane 14 can generally include a perimeter wall 76, an end wall 78, and an elongated wall 80. The membrane 14 can further include a tray receiving portion 82 and a stem receiving portion 84. The stem receiving portion 84 can have an outer wall 86 and an inner wall 88 (FIG. 7). The elongated wall 80 can provide fin receiving extension walls 90. The perimeter wall 76 and the end wall 78 can collectively define a first cavity portion 92. The elongated wall 80 can define a second cavity portion 94. The first and second cavity portions 92 and 94 can cooperate to define an implant receiving cavity 95. Vent ports 97 (FIG. 7) can be formed through the membrane 14. In some examples, the vent ports 97 can be located for aligning with the vent ports 53 (FIG. 7) in the mold body 30.

An inlet port 96 can be provided on the stem receiving portion 84 of the membrane 14. The inlet port 96 in the examples shown generally comprises female threads 98. Anti-rotation facets 99 can be formed on the inlet port 96. It will be understood, however, that the inlet port 96 can additionally or alternatively include other mounting structures suitable to couple with a full material delivery device. Furthermore, it will be appreciated that while the threads 98 have been shown associated with the membrane 14, threads may additionally or alternatively be formed on the mold body 30 at the inlet port 56. In such a configuration the mold 12 could be used without the membrane 14.

The membrane 14 can be formed of a generally flexible material such as silicone. The membrane 14 can be removably disposed on the inner surface 34 of the mold cavity 46. In this regard, the membrane 14 can be thin, flexible, and freely cement-releasing. The membrane 14 can include features to allow for easy separation from the doughy cement 28, such as thin sections, fine perforations, and/or a tear-starting notch or cut. The membrane 14 can have a low tear strength such as some silicone formulations. While not specifically shown, a vacuum port may be included in one or both of the mold 12 and membrane 14 to further improve the quality of the prosthesis-cement interface by eliminating or minimizing porosity at the prosthesis-cement interface. The vacuum port can also result in easier cement delivery, and reduced bone cement monomer vapors in the operating room environment.

In other embodiments, the mold 12 may be in the form of an open-topped mold/shell suitable for delivery of cement in a pre-dough state, and/or in a reduced viscosity state. The prosthetic implant 22 could be introduced to the tacky cement via the open top resulting in a geometry equivalent to, or several millimeters thicker than, that of the desired final cement mantle. In yet other examples, the mold 12 may be in the form of an open-topped mold/shell having a closed bottom. In such a configuration, the delivery of cement may be accomplished through the open top. Fill level markers or indicia may be provided on the mold to indicate when the appropriate amount of cement has been filled. The prosthetic implant can be subsequently introduced into the closed bottom mold. Vents can optionally be incorporated in the mold.

Figure 9:
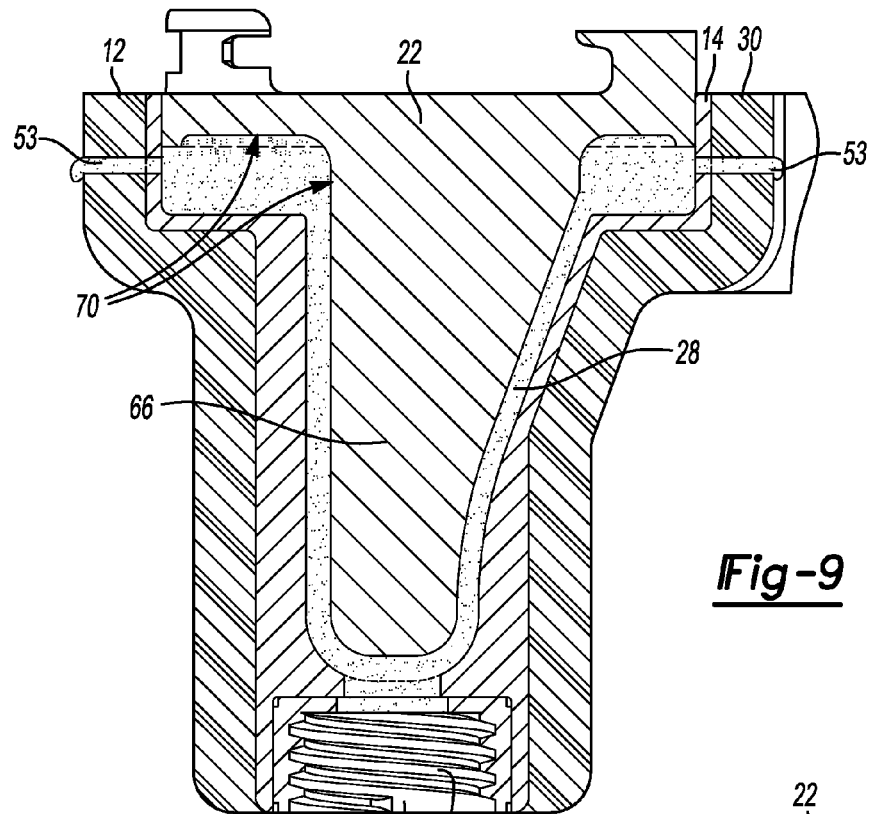

With particular reference now to FIGS. 7-9, an exemplary method of forming a flowable material 100 against the prosthetic implant 22 will be described. At the outset, the prosthetic implant 22 can be located generally into the implant receiving cavity 95 of the membrane 14. Once the prosthetic implant 22 has been sufficiently received into the implant receiving cavity 95, a void 106 can be created generally between the bone opposing surface 70 of the prosthetic implant 22 and the inner wall 88 of the membrane 14. In the position shown in FIG. 7, the stem 66 is received at least partially by the stem receiving portion 84 of the membrane 14. Similarly, the platform-like tray 64 is at least partially received by the first cavity portion 92 of the membrane 14.

It will be appreciated that the void 106 will be of a size and shape that will determine the shape and dimensions of the cement mantle applied to the implant 22 prior to implantation. In various embodiments, the shape of the void and resulting mantle will substantially conform to the profile of the implant. It is understood, though, that the dimensions of the void and resulting mantle may vary along the surface of the implant. In general, the void and resulting mantle may be from about 1 mm to about 15 mm, from about 2 mm, from about 10 mm, or from about 3 to about 7 mm, in depth. In embodiments with a first and second cavity portion, as discussed above, the void and resulting mantle in the first cavity portion may differ in dimension from the void and resulting mantle in the second cavity portion. For example, when the second cavity portion defines a stem, the void and resulting mantle in the second cavity portion may have a depth greater than that of the void and resulting mantle in the first cavity portion.

Next, a surgeon can couple a flowable material delivery device 120 generally to the inlet port 96 on the membrane 14. In the example shown, the flowable material delivery device 120 generally includes male threads 122 that can be configured to threadably mate with the threads 98 provided on the inlet port 96 of the membrane 14. Other configurations are contemplated. In one example, the flowable material delivery device 120 can be, or incorporate features of, an Optivac® vacuum mixing system offered by Biomet Manufacturing Corp. of Warsaw, Ind.

The exemplary flowable material delivery device 120 can generally include a syringe portion 123 and a plunger portion 124. Next, a surgeon can retain the prosthetic implant 22 generally within the implant receiving cavity 95 such as by a finger or other retaining measure. It is contemplated that the perimeter wall 36 of the mold body 30 can have an overhanging lip that may flexibly retain the tibial component 24 within the implant receiving cavity 95. Nevertheless, once the prosthetic implant 22 is suitably retained within the implant receiving cavity 95, a surgeon can depress the plunger 124 causing the flowable material (i.e., bone cement) 100, still in a relatively low viscosity state, through the inlet port 56 of the mold body 30, and through the inlet port 96 of the membrane 14 and into the void 106 (see FIG. 8).

During advancement of the flowable material 100 into the void 106, air 130 that was present within the void 106 can be urged through the respective vents 98 and 53. Injection of the flowable material 100 is continued until a suitable amount of flowable material 100 has been deployed. It is contemplated, that in some examples, the flowable material 100 can be continued to be advanced into the void 106 until the surgeon observes flowable material 100 being expelled through the ports 53. In this regard, the surgeon continues the introduction of the flowable material 100 such that the flowable material 100 is sufficiently located in contact with the bone opposing surface 70 of the prosthetic implant 22.

The surgeon may then decouple the flowable material delivery device 120 from the inlet port 96 as shown in FIG. 9. The surgeon can then wait a predetermined amount of time until the flowable material reaches a suitable viscosity (higher than the viscosity of the flowable material 100 during introduction into the void 106). It will be appreciated that the viscosity will vary over time, subject to the composition of the flowable material (e.g., composition of the cement) and curing conditions (e.g., temperature). The predetermined time may be any time acceptable in clinical practice, and may depend on such factors as the composition of the flowable material (e.g., cement), the implant, the condition of the bone into which the implant is to be inserted, and surgical clinical conditions and procedures. In some embodiments, wherein a cement having a relatively high viscosity is used, the predetermined time is from about 1 to about 3 minutes after initial mixing of cement components and injection into the mold. In general, the viscosity after the predetermined time will approximate a dough, which is not substantially flowable, but is deformable with application of pressure by manual manipulation of the material, which may be aided using tools and devices, consistent with acceptable clinical practice.

Figure 10:
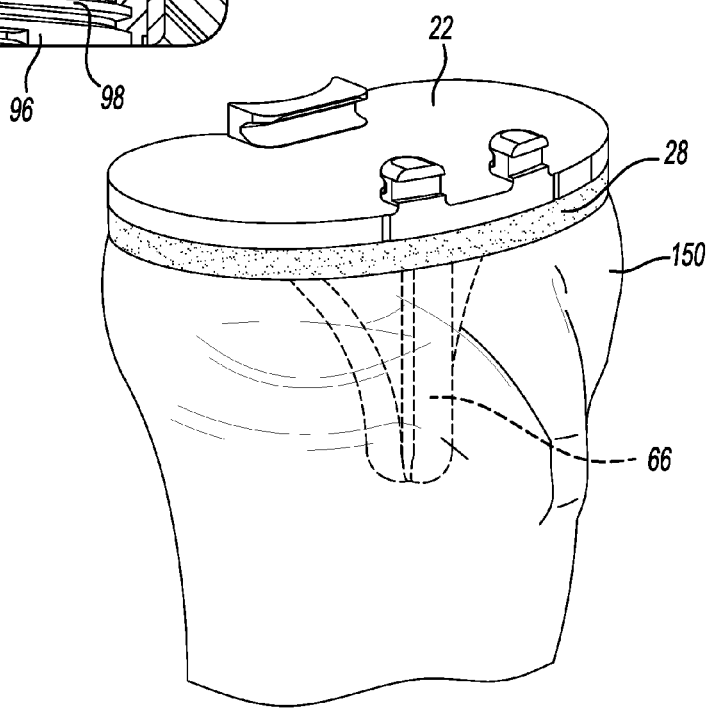
FIG. 10 is an anterior perspective view of an exemplary tibia of which the prosthetic implant and resulting dough-like structure are implanted.

It is contemplated that a surgeon can be satisfied once a dough-like structure 28 has sufficiently adhered to the bone opposing surface 70 of the prosthetic implant 22. In other words, after the viscosity of the flowable material 100 has increased and the surface tackiness has decreased to a point that a surgeon could comfortably place and immediately clean up excess flowable material 100 extruded from between the implant 22 and bone during placement of the implant 22, the prosthetic implant 22 and dough-like structure 28 can collectively be removed from the membrane 14 and mold 12. The resultant structure can then be implanted into a prepared tibia 150 as illustrated in FIG. 10.

In other examples, the mold 12 of the kit 20 might function as a part of a sterile packaging of the prosthetic implant 22. Moreover, the kit 20 may also include a shield that could be deployed to inhibit cement contact with a portion of the prosthetic implant 22 which will oppose bone (i.e., the bone opposing surface 70) and/or otherwise may be coated with the flowable material 100. An example of such a shield would be a thin silicone (or other polymeric material) coating/shield/dam that may be slipped over the fins 68 of the stem 66 prior to application of the flowable material 100 to the bone opposing surface 70 of the prosthetic implant 22.

According to features of the instant application, the quality and/or strength of the prosthesis-cement interface is improved via advanced adhesion and micro-interlock through earlier (tackier/lower viscosity) prosthesis-cement contact. The interface quality would also be protected from contamination in several device embodiments. The quality of the cement-bone interface would also benefit according to the teachings of the present disclosure as compared to earlier techniques as the surface of the cement applied to the prosthetic implants prior to placement in the bone are not exposed to air, and thus will not dry out causing a leathery skin to be formed, which is not well-suited to interdigitation with the bone.

Figure 11:
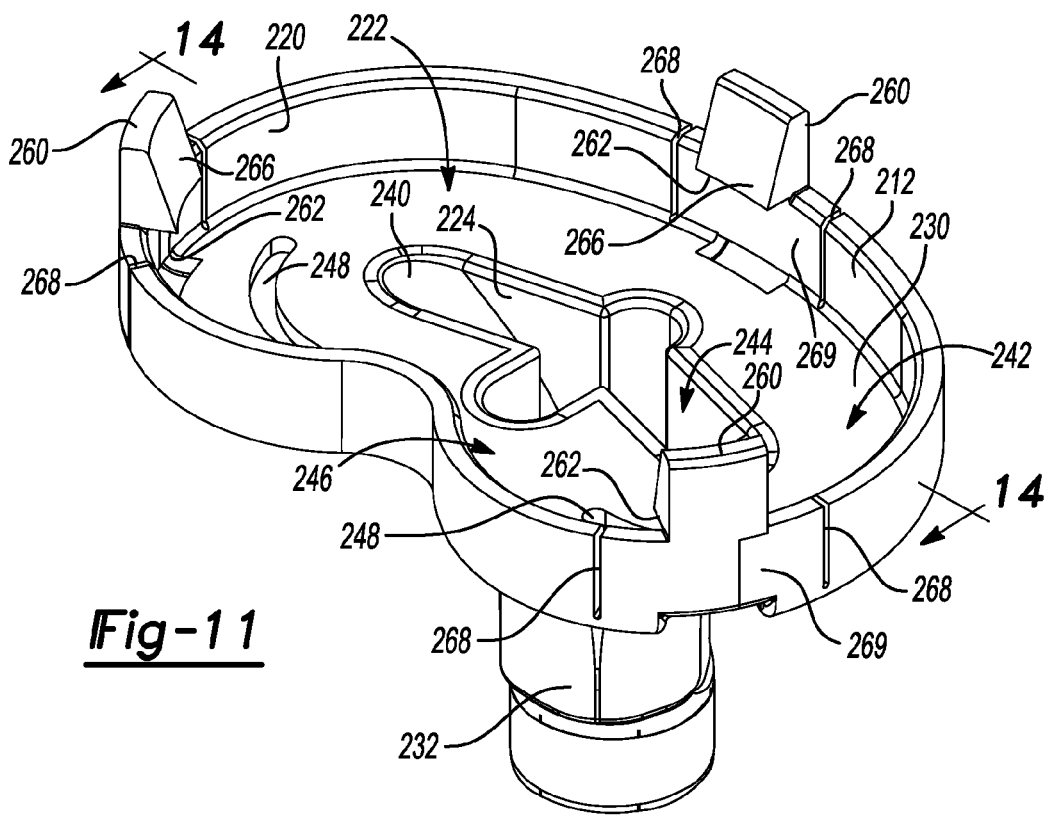
FIG. 11 is a top perspective view of a mold constructed in accordance to additional features of the present disclosure.
Figure 12:
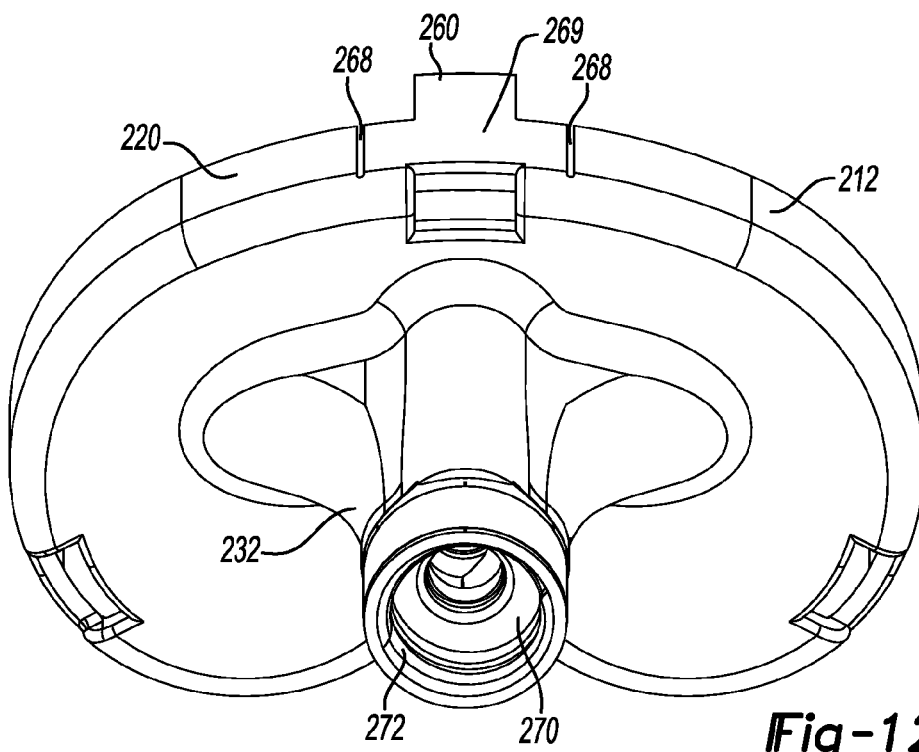
FIG. 12 is a bottom perspective view of the mold of FIG. 11.
Figure 13:
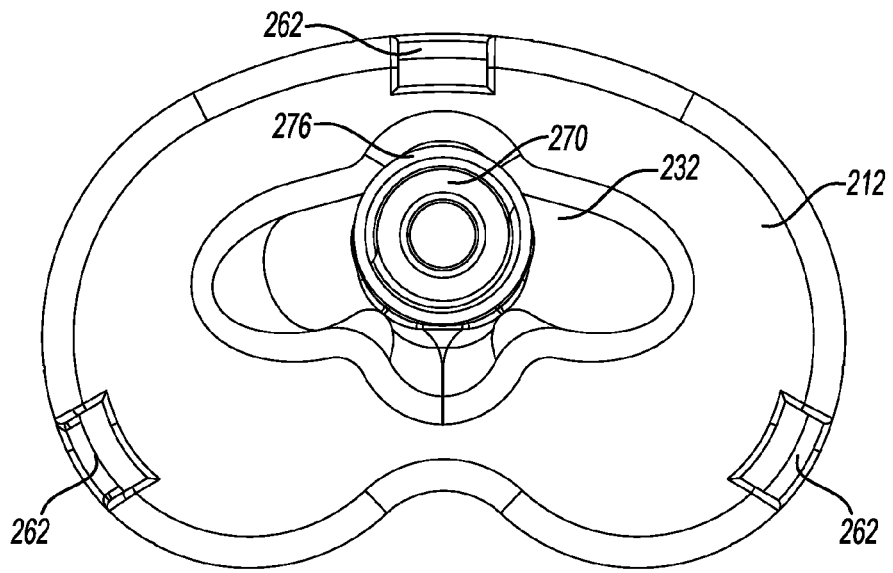
FIG. 13 is a bottom plan view of the mold of FIG. 11.
Figure 14:
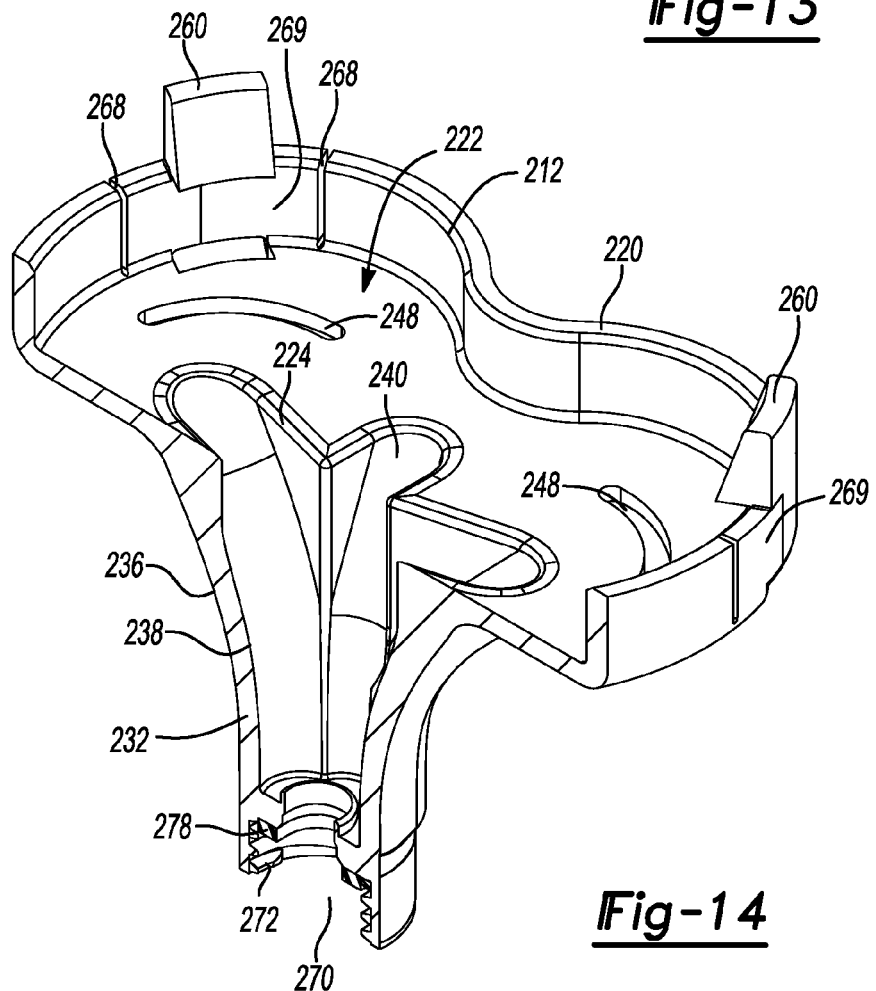
FIG. 14 is a sectional view taken along lines 14-14 of FIG. 11.
Figure 17:
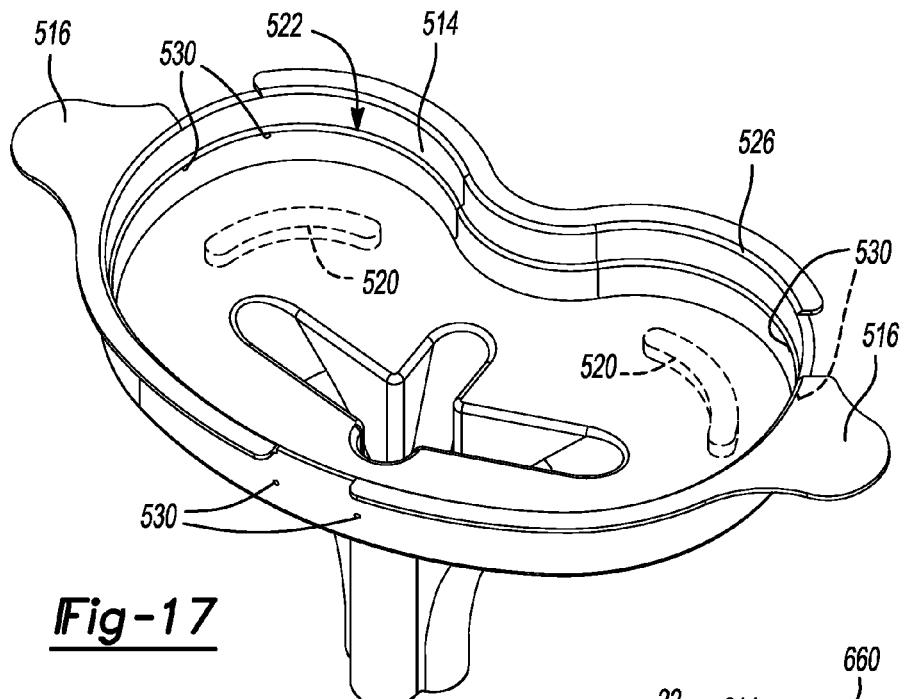
FIG. 17 is a front perspective view of a membrane according to additional features of the present disclosure.
Figure 18:
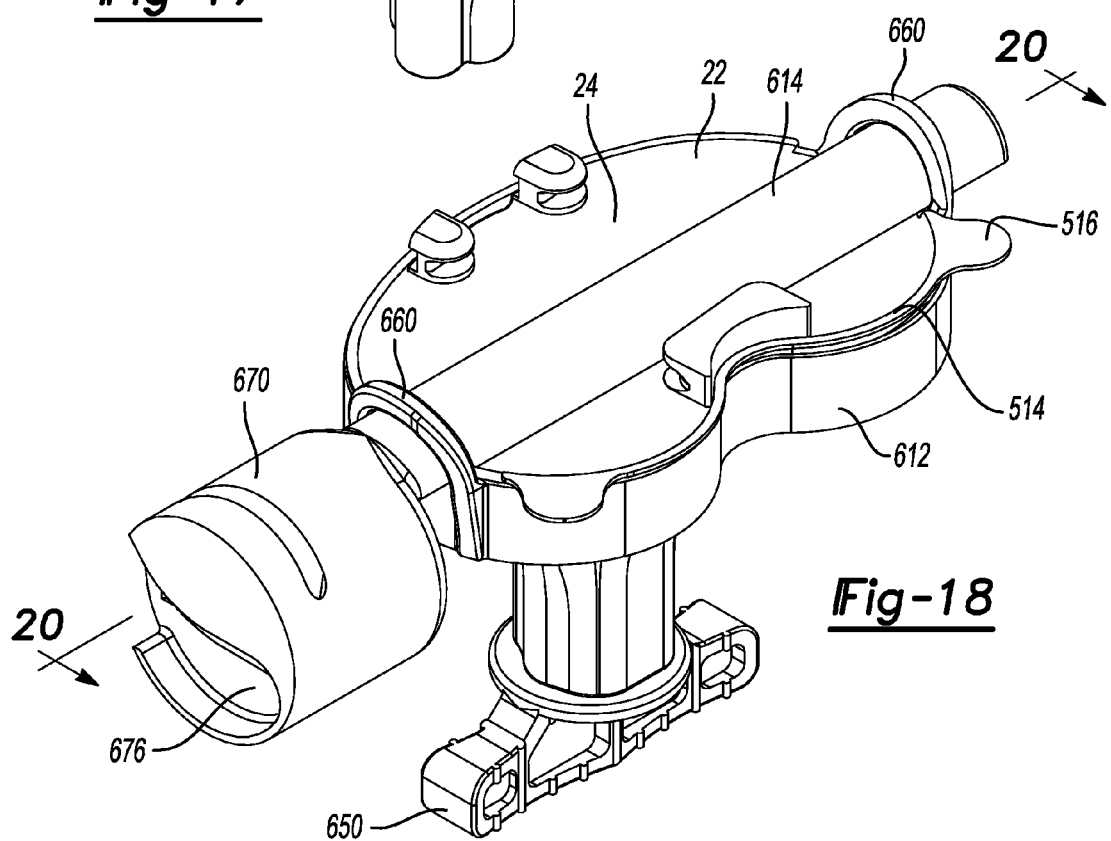
FIG. 18 is a perspective view of an exemplary mold and a locking bar according to other features of the present disclosure.
Figure 19:
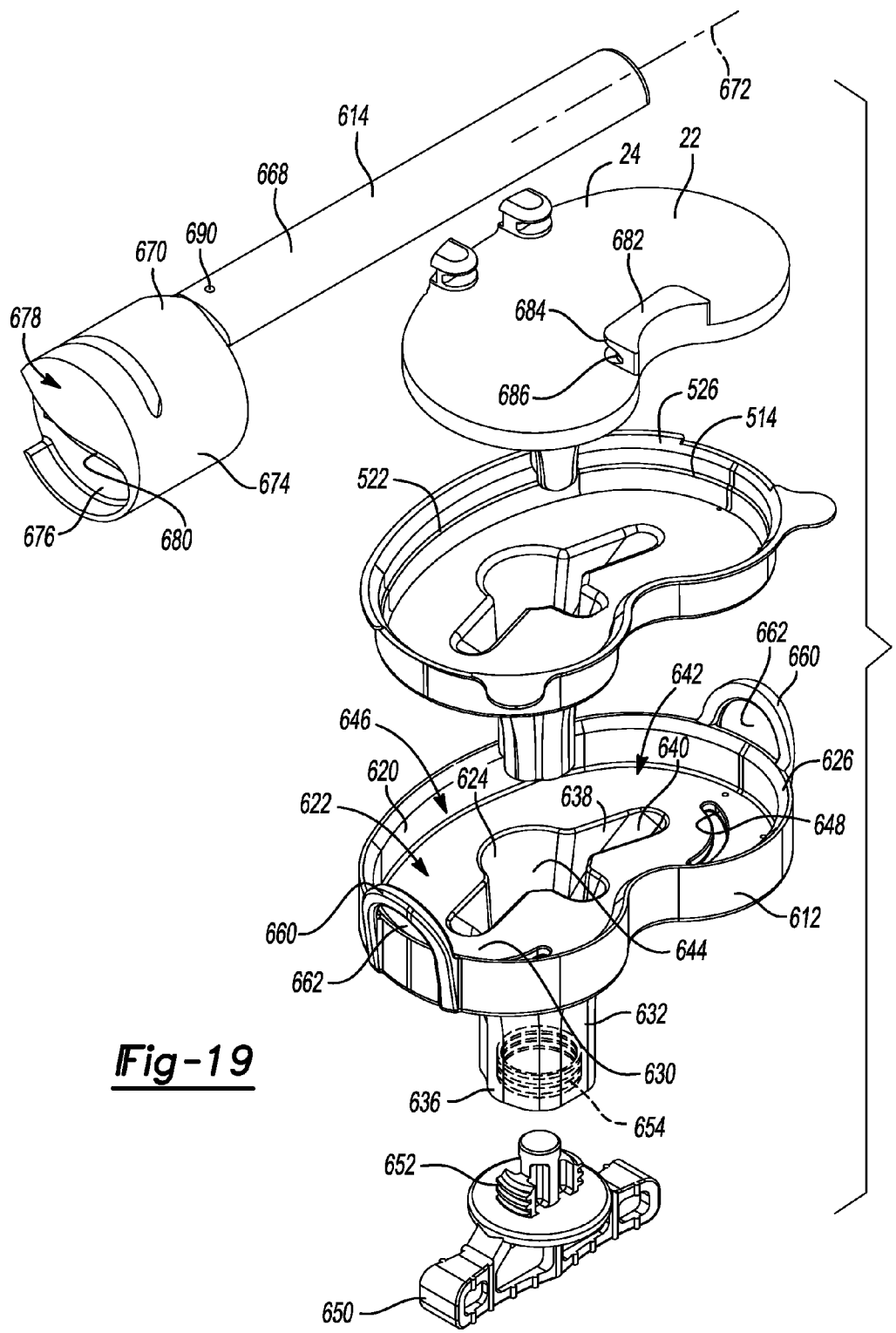
FIG. 19 is an exploded perspective view of the mold, locking bar, tibial component and membrane of FIG. 18.
Figure 20:
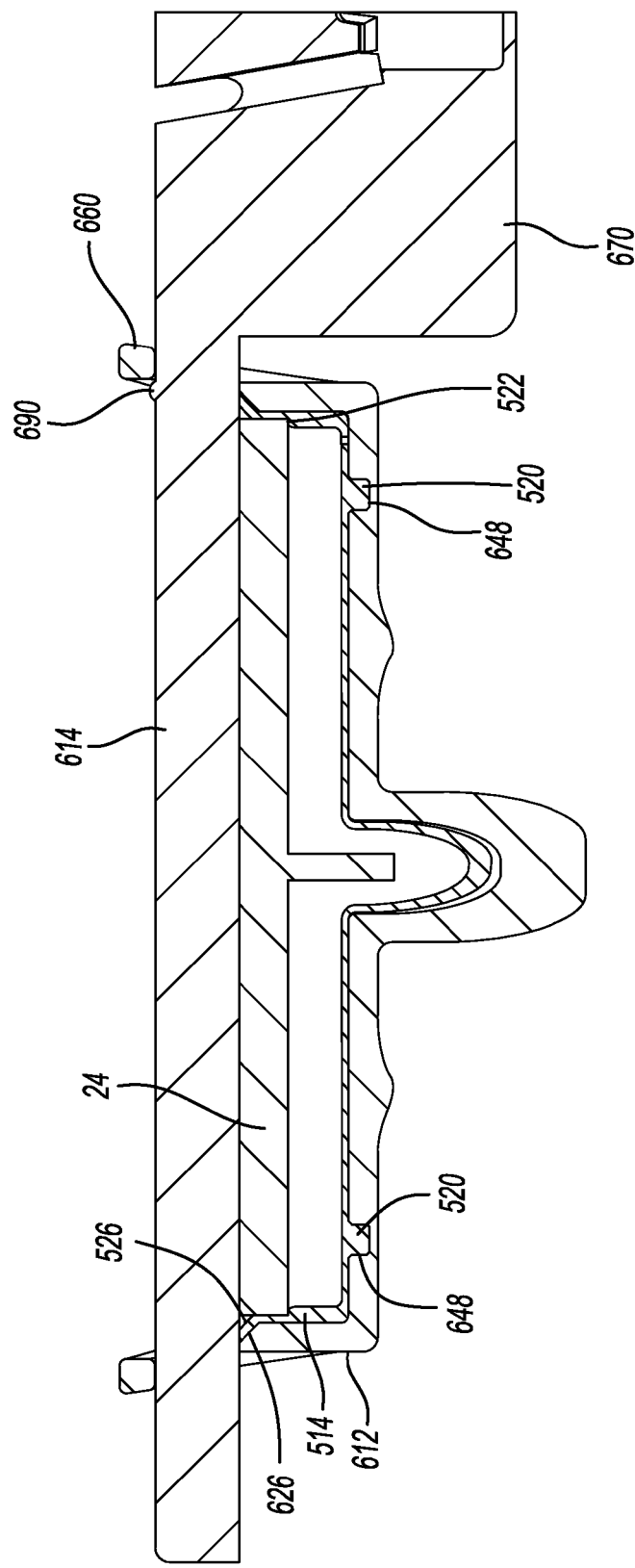
FIG. 20 is a cross-sectional taken along lines 20-20 of FIG. 18.

With reference now to FIGS. 11-14, a mold constructed in accordance to additional features of the present disclosure is shown and generally identified at reference numeral 212. Unless otherwise described herein, the mold 212 may be used in combination with the other components of the kit 20 described above. The mold 212 can generally include a perimeter wall 220, an end wall 222, and an elongated wall 224. The mold 212 can further include a tray receiving portion 230 and a stem receiving portion 232. The stem receiving portion 232 can have an outer wall 236 and an inner wall 238 (FIG. 14). The elongated wall 224 can provide fin receiving extension walls 240. The perimeter wall 220 and the end wall 222 can collectively define a first cavity portion 242. The elongated wall 224 can define a second cavity portion 244 (FIG. 11). The first and second cavity portions 242 and 244 can cooperate to define an implant receiving cavity 246. Female receiving portions 248 can be formed into the end wall 222 of the mold 212. In the example shown, the female receiving portions 248 are generally crescent shaped for receiving a complementary geometry extending from a membrane 514 (FIGS. 17 and 20). The resulting interfitting structure can prevent membrane wrinkling or displacement within the mold. The perimeter wall 220 can further include a series of tabs 260 extending therefrom. The tabs 260 can each generally include an engaging lip 262 that is configured to selectively retain the tibial component 24 within the implant receiving cavity 246. A pair of slits 268 is formed into the perimeter wall 220 on opposite sides of tab sections 269 located under each of the tabs 260. The slits 268 can facilitate breaking away of the tabs 260 and tab sections 269 prior to removal of the implant 22 and resultant dough-like structure 28 from the mold 212. The slits 268 can further provide an escape path for trapped air within the first cavity portion 242.

An inlet port 270 can be provided on the stem receiving portion 232 of the mold 212. The inlet port 270 can include female threads 272. A gasket such as a silicone O-ring 278 may be disposed at the inlet port 270 to allow an unthreaded nozzle to be sealably butted (or positioned) against the gasket during mold filling. In some examples, the gasket can be conically shaped to aid in centering of a flowable material delivery device 120.

Figure 15:
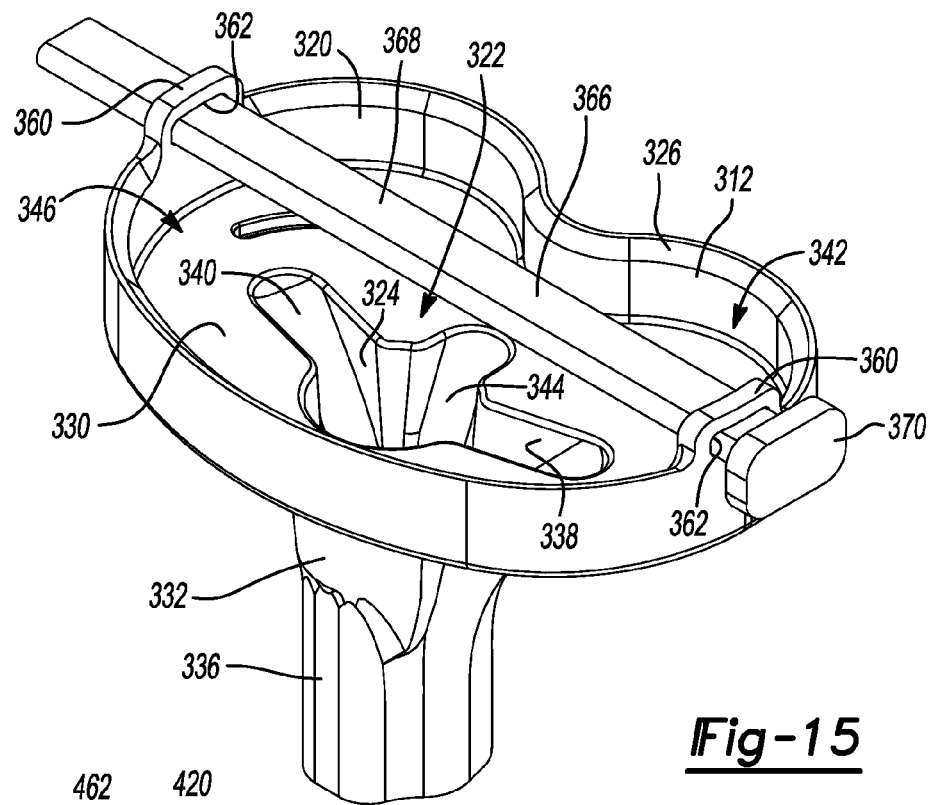
FIG. 15 is a top perspective view of a mold constructed in accordance to additional features of the present disclosure.

With reference now to FIG. 15, a mold constructed in accordance to additional features of the present disclosure is shown and generally identified at reference numeral 312. Unless otherwise described herein, the mold 312 may be used in combination with the other components of the kit 20 described above. The mold 312 can generally include a perimeter wall 320, an end wall 322, and an elongated wall 324. An angled wall 326 can cooperatively receive an angled wall on a membrane as will become appreciated. The mold 312 can further include a tray receiving portion 330 and a stem receiving portion 332. The stem receiving portion 332 can have an outer wall 336 and an inner wall 338. The elongated wall 324 can provide fin receiving extension walls 340. The perimeter wall 320 and the end wall 322 can collectively define a first cavity portion 342. The elongated wall 324 can define a second cavity portion 344. The first and second cavity portions 342 and 344 can cooperate to define an implant receiving cavity 346. The perimeter wall 320 can further include a pair of ears 360 extending therefrom. The ears 360 can define passages 362 therethrough. The passages 362 of the ears 360 can be configured to slidably receive a locking bar 366. According to one example, the locking bar 366 can include a shaft portion 368 and a head portion 370. The shaft portion 368 can be slidably advanced through the respective passages 362 in the ears 360 to retain the tray such as tray 22, (not specifically shown) within the first and second cavity portions 342 and 344 of the implant receiving cavity 346. In this regard, the locking bar 366 can maintain the tray within the implant receiving cavity 346 during advancement of the flowable material between the mold 312 and the tray 22.

Figure 16:
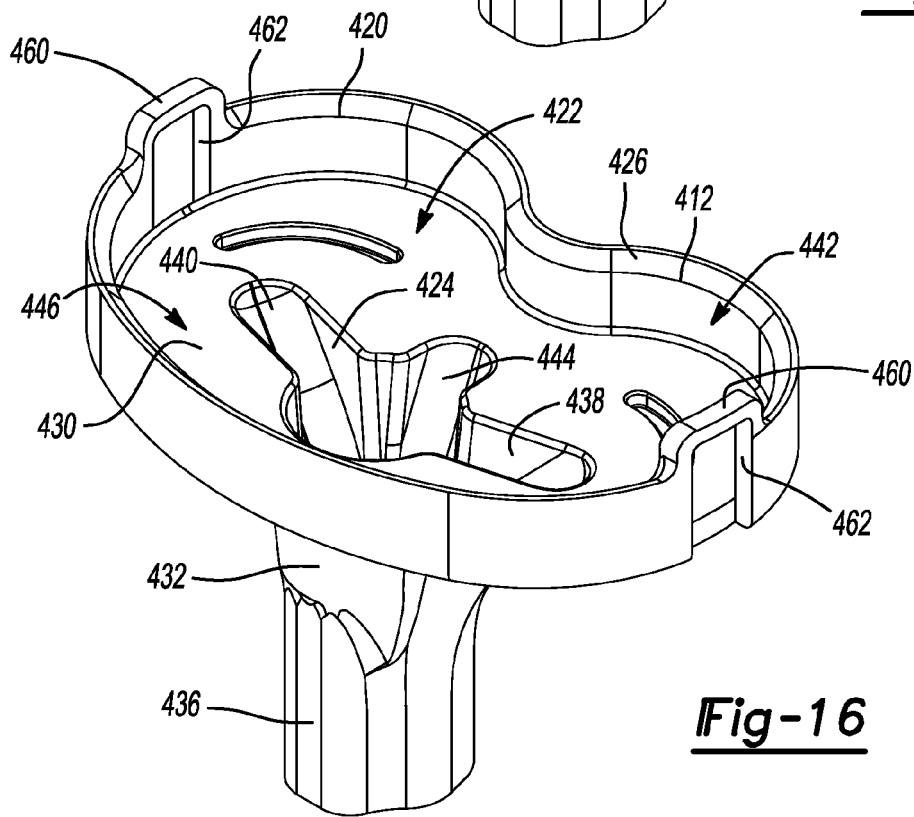
FIG. 16 is a top perspective view of a mold constructed in accordance to additional features of the present disclosure.

With reference now to FIG. 16, a mold constructed in accordance to additional features of the present disclosure is shown and generally identified at reference numeral 412. Unless otherwise described herein, the mold 412 may be used in combination with the other components of the kit 20 described above. The mold 412 can generally include a perimeter wall 420, an end wall 422, and an elongated wall 424. An angled wall 426 can cooperatively receive an angled wall on a membrane as will become appreciated. The mold 412 can further include a tray receiving portion 430 and a stem receiving portion 432. The stem receiving portion 432 can have an outer wall 436 and an inner wall 438. The elongated wall 424 can provide fin receiving extension walls 440. The perimeter wall 420 and the end wall 422 can collectively define a first cavity portion 442. The elongated wall 424 can define a second cavity portion 444. The first and second cavity portions 442 and 444 can cooperate to define an implant receiving cavity 446. The perimeter wall 420 can further include a pair of ears 460 extending therefrom. The ears 460 can define passages 462 therethrough. The passages 462 of the ears 460 can be configured to slidably receive a locking bar (such as the locking bar 366).

With reference to FIG. 17, a membrane 514 according to additional features of the present disclosure is shown. The membrane 514 can be formed of flexible material such as silicone. The membrane 514 may provide similar material characteristics as the membrane 14 described above. The membrane 514 can incorporate flaps 516 thereon for facilitating removal of the dough-like structure 28 and prosthetic implant 22 from the mold 212, 312 or 412 subsequent to sufficient adhering of the dough-like structure 28 onto the prosthetic implant 22. The membrane 514 is then removed. The resultant structure can then be implanted into a tibia such as the tibia 150 illustrated in FIG. 10. The membrane 514 can include positively extending male insertion portions 520 configured to be nestingly received by the female receiving portions 248 on the mold 212. The membrane 514 can include a ledge 522 configured therearound for positively locating and receiving the tibial component 24 (FIG. 20). An angled wall 526 can be provided around the membrane 514 to guide the tibial component 24 toward placement onto the ledge 522. Vents 530 can be formed through the membrane 514.

With reference now to FIGS. 18-23, a mold constructed in accordance to additional features of the present disclosure is shown and generally identified at reference numeral 612. As will become appreciated from the following discussion, the mold 612 can be used in combination with a locking bar 614 to retain the tray 22 in the mold 612 during advancement of the flowable material 100 (see also FIG. 9). The locking bar 614 can be subsequently used to aid in withdrawal of the tray 22 and membrane 514 from the mold 612 (see FIG. 22). Unless otherwise described herein, the mold 612 may be used in combination with the other components of the kit 20 described above. The mold 612 can generally include a perimeter wall 620, an end wall 622, and an elongated wall 624. An angled wall 626 can cooperatively receive the angled wall 526 on the membrane 514. The mold 612 can further include a tray receiving portion 630 and a stem receiving portion 632. The stem receiving portion 632 can have an outer wall 636 and an inner wall 638. The elongated wall 624 can provide fin receiving extension walls 640. The perimeter wall 620 and the end wall 622 can collectively define a first cavity portion 642. The elongated wall 624 can define a second cavity portion 644. The first and second cavity portions 642 and 644 can cooperate to define an implant receiving cavity 646. Female receiving portions 648 can be formed into the end wall 622 of the mold 612. The female receiving portions 648 can be shaped to receive the male insertion portions 520 on the membrane 514. A plug 650 having threads 652 can threadably mate with complementary threads 654 on the mold 612 (or any of the other molds disclosed herein). The plug 650 can be inserted subsequent to the introduction of flowable material into the mold 612 to keep the flowable material in the mold 612 during curing. The perimeter wall 620 of the mold 612 can further include a pair of ears 660 extending therefrom. The ears 660 can define the passages 662. In the example shown, the ears 660 can generally provide the shape of a half-cylinder. The passages 662 of the ears 660 can be configured to slidably receive the locking bar 614.

According to the example shown, the locking bar 614 can include a shaft portion 668 and an engagement head 670. In one example, the shaft portion 668 can generally take the shape of a half-cylinder that extends along a longitudinal axis 672. The engagement head 670 generally comprises a cylindrical body portion 674 that incorporates an arcuate groove 676 into an end face 678. A lip 680 (see also FIG. 23) can be formed on the cylindrical body portion 674 adjacent the groove 676. As will become appreciated from the following discussion, the groove 676 and lip 680 can cooperate to engage complementary structure provided on a posterior tab 682 extending from the prosthetic implant 22. The posterior tab 682 can include an overhang 684 that further defines a groove 686 into the posterior tab 682 (see FIG. 19).

An exemplary sequence of using the mold 612 and locking bar 614 according to one example of the present disclosure will now be described. With initial reference to FIG. 20, the locking bar 614 may be slidably advanced through the respective passages 662 of the ears 660. In one example, the locking bar 614 can be advanced in a direction leftward as viewed in FIG. 20 a distance until a nub 690 on the locking bar 614 locates beyond the ears 660. As can be appreciated, the nub 690 can further secure the locking bar 614 into an installed position and may also provide tactile feedback to a user that a satisfactory assembled position has been attained. Next, the flowable material 100 can be advanced into the mold 612 such as described above. Once the surgeon is satisfied that the flowable material 100 has cured sufficiently, the user may pull the locking bar 614 away from the ears 660 (in a direction rightward as viewed from FIG. 20).

Figure 21:
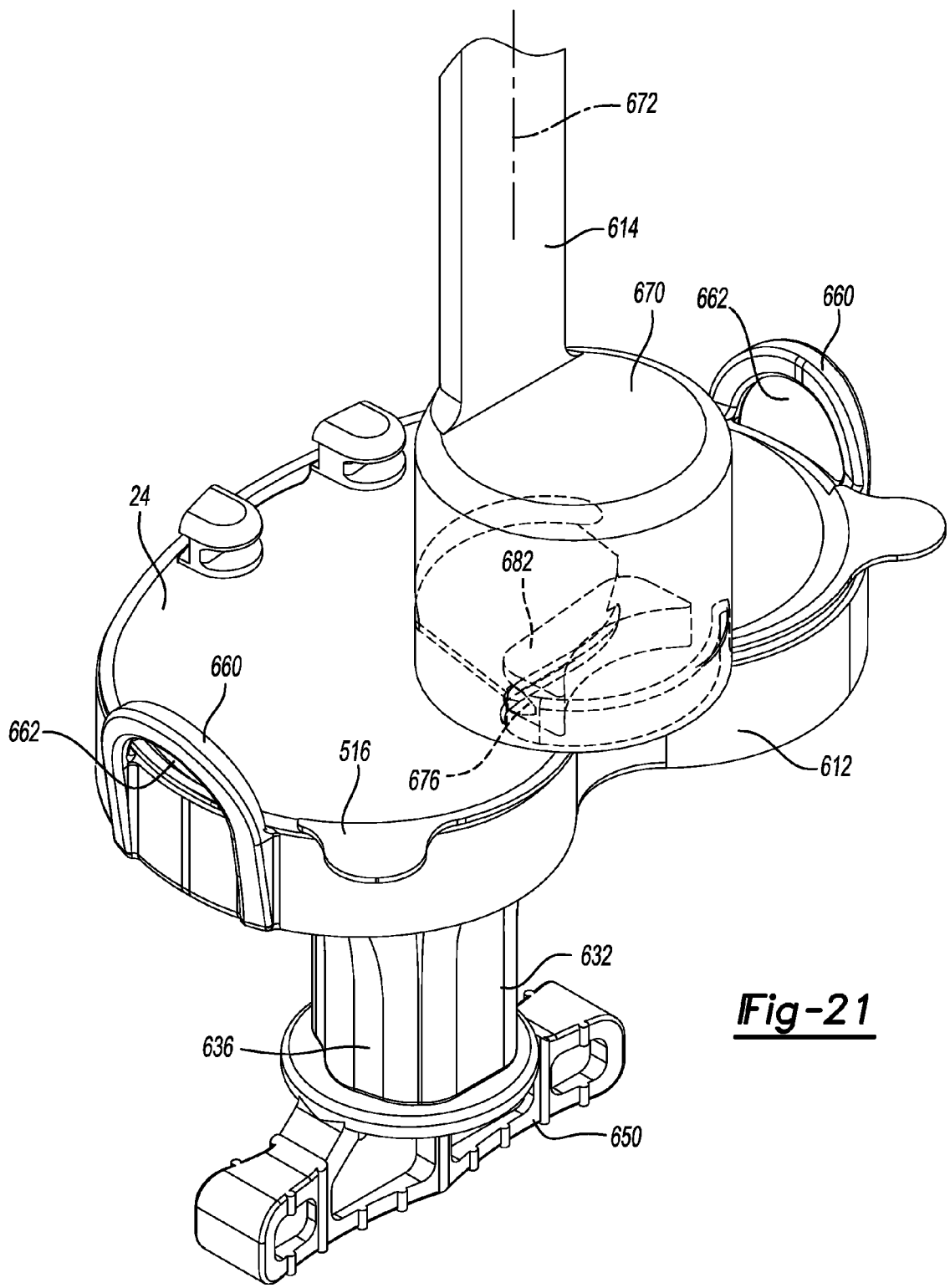
FIG. 21 is a perspective view of the mold and tibial component of FIG. 18 and shown with the locking bar engaged to the tibial component for withdrawal of the tibial component from the mold.
Figure 22:
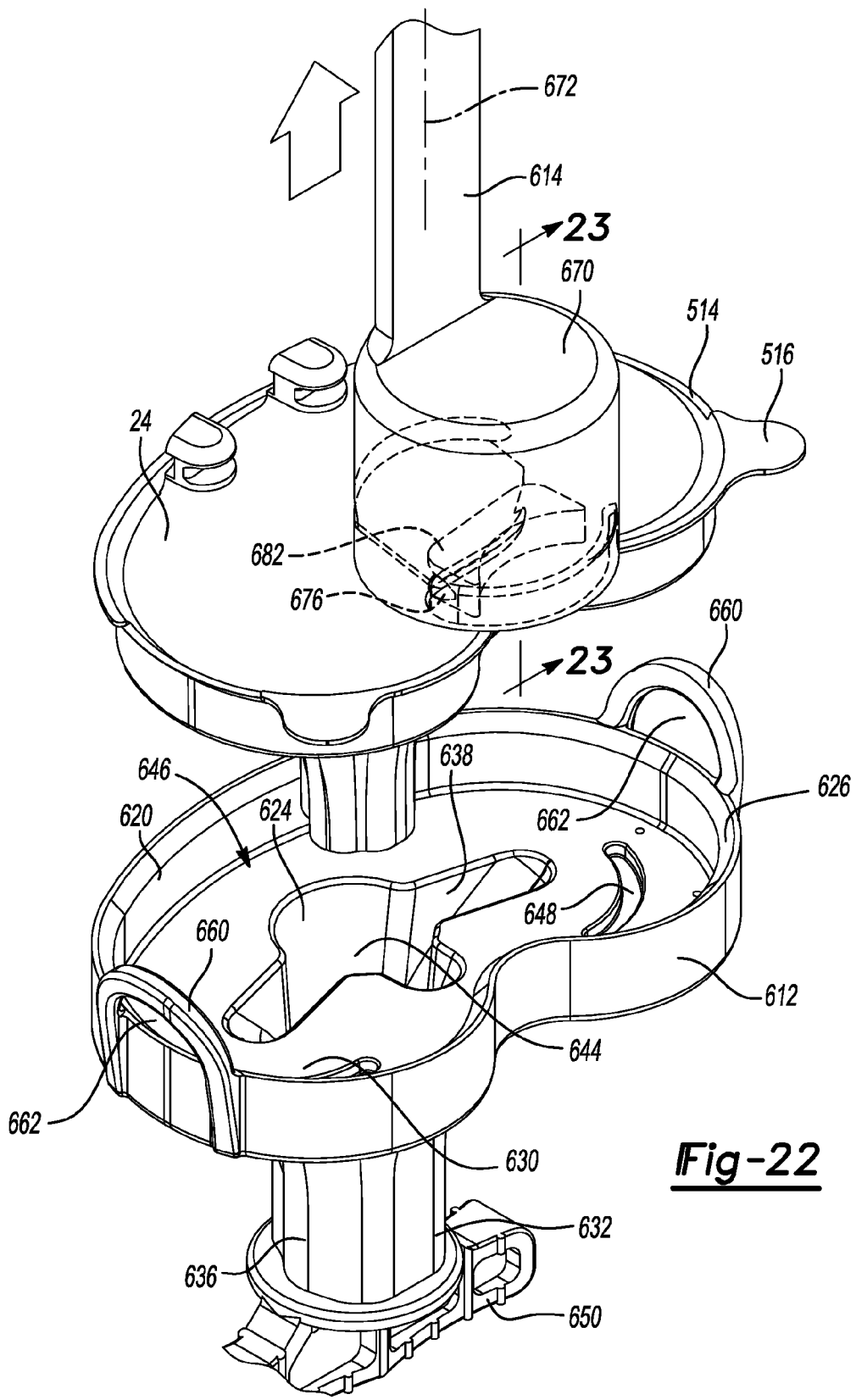
FIG. 22 is a perspective view of the mold, tibial component and locking bar of FIG. 21 and shown subsequent to withdrawal of the tibial tray from the mold.
Figure 23:
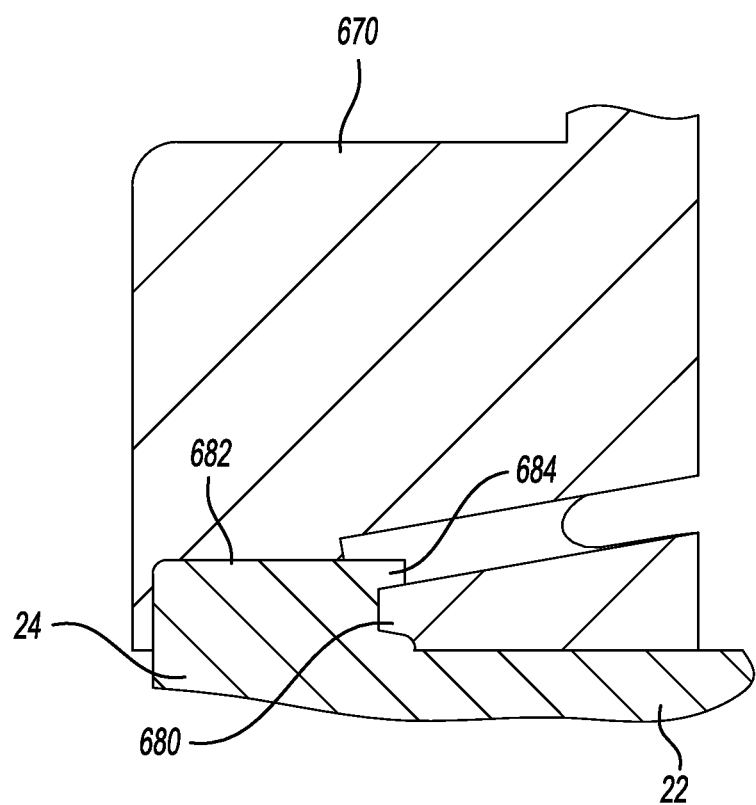
FIG. 23 is a cross-sectional view of the engagement head on the locking bar and posterior tab of the tibial component taken along lines 23-23 of FIG. 22.

Turning now to FIG. 21, a user can rotate the locking bar 614 on end to align the engagement head 670 with the posterior tab 682 on the tibial component 24. More specifically, the user may slidably rotate the engagement head 670 such that the groove 676 in the engagement head 670 slidably negotiates into engagement with the posterior tab 682. Explained further, the user can rotate the locking bar 614 such that the lip 680 on the engagement head 670 locates generally under the overhang 684 of the posterior tab 682 (see also in FIG. 23). Once the locking bar 614 has suitably engaged the posterior tab 682 on the tibial component 24, the user may advance the locking bar 614 in a direction upward along the axis 672 as illustrated in FIG. 22. The locking bar 614 can therefore be used to impart a removal force onto the tibial component 24 to withdraw the tibial component 24 from the mold 612. In the example shown, the membrane 514 is also removed (such as peeled) from the mold 612, however, in some examples the membrane 514 may be held into the mold 612 such as at the flaps 516. The locking bar 614 can additionally be used to position the tibial component 24 such as during implanting. Such a configuration may be particularly advantageous as a surgeon can avoid touching the cured cement.

Figure 24:
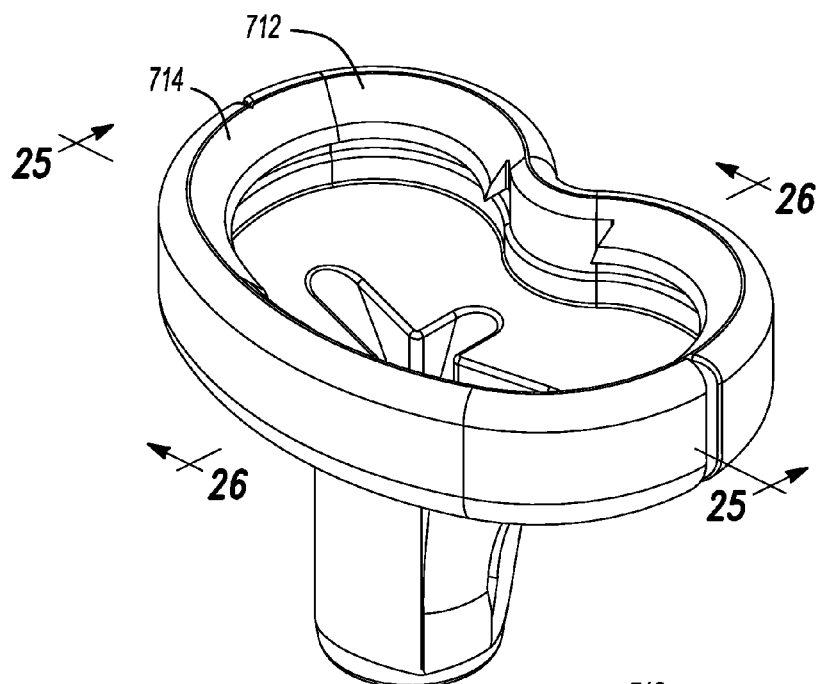
FIG. 24 is a top perspective view of a mold constructed of silicone in accordance to additional features of the present disclosure.
Figure 25:
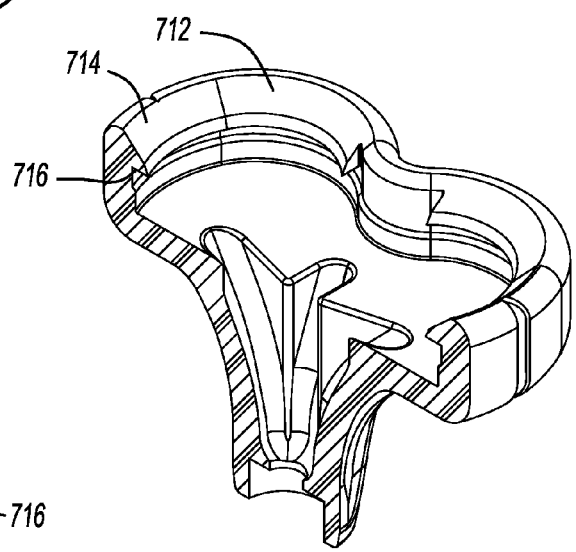
FIG. 25 is a cross-sectional view taken along lines 25-25 of FIG. 24.
Figure 26:
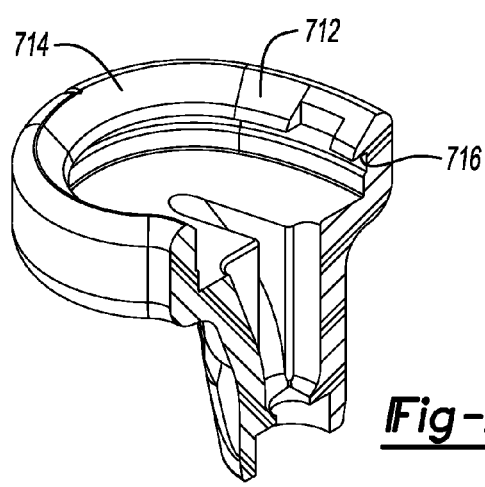
FIG. 26 is a cross-sectional view taken along lines 26-26 of FIG. 24.

Turning now to FIGS. 24-26, a mold constructed in accordance to additional features of the present disclosure is shown and generally identified at reference numeral 712. The mold 712 is constructed entirely of silicone. A ramp 714 is formed around a perimeter of the mold and leads to a lip 716. The lip 716 can hold the implant during introduction of flowable material. The silicone material is manually displaceable such that a surgeon or medical technician can pull back the lip 716 from the implant subsequent to curing of the flowable material.

In any of the examples described herein, a mask or other thin, temporary barrier structure can be provided against the stem 66 to preclude flowable material 100 from contacting the stem 66 while still allowing the flowable material 100 to engage (and cure against) the inferior surface of the platform-like tray 66 of the tibial component 24.

Non-Limiting Discussion of Terminology:

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

What is claimed is:

1. An apparatus for forming a flowable material against a prosthetic implant, the apparatus comprising:
    a mold body having an outer surface and an inner surface; the inner surface defining a mold cavity that is selectively configured to at least partially accept the prosthetic implant in a forming position, and having a pair of ears that define passages and extend from a perimeter wall of the mold body;
    a locking bar that is removably received into the passages;
    a membrane removably disposed on the inner surface defining the mold cavity;
    wherein the mold cavity substantially conforms to a profile of a bone opposing surface of the prosthetic implant such that a void is created between the membrane and the bone opposing surface of the prosthetic implant;
    a first inlet port configured on the mold body that extends between the inner and outer surfaces; and
    a second inlet port configured on the membrane that extends between the first inlet port configured on the mold body and the void;
    wherein the first and second inlet ports are configured to permit introduction of the flowable material into the void and against the bone opposing surface of the prosthetic implant.

2. The apparatus of claim 1 wherein the mold body further defines at least one vent formed through the inner and outer surfaces, the at least one vent configured to permit air to escape therethrough upon the introduction of the flowable material into the void.

3. The apparatus of claim 1 wherein the mold body comprises one of polyethylene, polycarbonate, polyethylene terephthalate (PET), polypropylene or silicone.

4. The apparatus of claim 1 wherein the mold body comprises at least one tab extending from the perimeter wall thereof, the at least one tab having an engaging lip configured to engage the prosthetic implant and maintain the prosthetic implant within the mold cavity during the introduction of the flowable material.

5. The apparatus of claim 4 wherein the perimeter wall of the mold body defines slits on opposite sides of the at least one tab, wherein the slits facilitate the at least one tab from being selectively broken away from a remainder of the mold body.

6. The apparatus of claim 1, further comprising a plug that selectively mates with the first inlet port.

7. The apparatus of claim 1 wherein the mold body is transparent.

8. The apparatus of claim 1 wherein the locking bar further comprises a shaft and an engagement head wherein the engagement head comprises structure that selectively engages complementary structure provided on the prosthetic implant for one of imparting a removal force onto the prosthetic implant from the mold body and positioning the prosthetic implant into the mold body.

9. The apparatus of claim 8 wherein at least one of the mold body and membrane includes a vacuum port formed therethrough.

10. The apparatus of claim 1 wherein the membrane is flexible.

11. The apparatus of claim 10 wherein the membrane comprises at least one of a slit, thin section, perforations, and a tear-starting notch.

12. The apparatus of claim 11 wherein the membrane comprises at least one flap extending from a periphery and configured to facilitate removal of the membrane from one of the mold body and the prosthetic implant.

13. The apparatus of claim 10 wherein the membrane is formed of silicone.

14. The apparatus of claim 1 wherein the mold cavity further comprises a first cavity portion having a geometry corresponding to a first feature of the prosthetic implant and a second cavity portion having a geometry corresponding to a second feature of the prosthetic implant.

15. The apparatus of claim 14 wherein the prosthetic implant comprises a tibial tray and wherein the first feature comprises a platform portion of the tibial tray and the second feature comprises a stem of the tibial tray.

16. The apparatus of claim 1 wherein the flowable material comprises bone cement.

17. A kit comprising the apparatus of claim 1, the kit further comprising:
    the prosthetic implant having the bone opposing surface; and
    the first inlet port configured on the mold body that extends between the inner and outer surfaces;
    wherein the first inlet port is configured to permit introduction of the flowable material into the void and against the bone opposing surface of the prosthetic implant.

18. The kit of claim 17; further comprising the membrane removably disposed on the inner surface of the mold cavity.

19. The kit of claim 17 wherein the mold cavity further comprises a first cavity portion having a geometry corresponding to a first feature of the prosthetic implant and a second cavity portion having a geometry corresponding to a second feature of the prosthetic implant.

20. The kit of claim 19 wherein the prosthetic implant comprises a tibial tray and wherein the first feature comprises a platform portion of the tibial tray and the second feature comprises a stem of the tibial tray.

* * * * *

UNITED STATES PATENT AND TRADEMARK OFFICE
CERTIFICATE OF CORRECTION

PATENT NO. : 9,944,000 B2
APPLICATION NO. : 14/117482
DATED : April 17, 2018
INVENTOR(S) : Smith et al.

It is certified that error appears in the above-identified patent and that said Letters Patent is hereby corrected as shown below:

In the Claims

Column 13, Line 25, Claim 1, delete "surface;" and insert --surface,-- therefor

Column 14, Line 52, Claim 18, delete "claim 17;" and insert --claim 17,-- therefor Signed and Sealed this
Fourth Day of June, 2019

Andrei Iancu
*Director of the United States Patent and Trademark Office*